US005585371A

United States Patent [19]

Lardy

[11] Patent Number: 5,585,371

[45] Date of Patent: Dec. 17, 1996

[54] TREATMENT OF IMMUNE SYSTEM WITH Δ5-ANDROSTENES

[75] Inventor: Henry A. Lardy, Madison, Wis.

[73] Assignee: Humanetics Corporation, St. Louis Park, Minn.

[21] Appl. No.: 189,917

[22] Filed: Feb. 2, 1994

Related U.S. Application Data

[63] Continuation-in-part of Ser. No. 922,850, Jul. 31, 1992, Pat. No. 5,292,730, which is a continuation-in-part of Ser. No. 867,288, Apr. 10, 1992, Pat. No. 5,296,481, which is a continuation of Ser. No. 575,156, Aug. 29, 1990, abandoned.

[51] Int. Cl.$^6$ ..................................................... A61K 31/56
[52] U.S. Cl. .................................................................. 514/171
[58] Field of Search ............................ 514/171; 424/93

[56] References Cited

U.S. PATENT DOCUMENTS

| | | | |
|---|---|---|---|
| 4,511,511 | 4/1985 | Lewbart | 260/239.55 |
| 4,518,595 | 5/1985 | Coleman et al. | 514/178 |
| 4,548,922 | 10/1985 | Carey et al. | 514/4 |
| 4,666,898 | 5/1987 | Coleman et al. | 514/177 |
| 4,746,508 | 5/1988 | Carey et al. | 424/88 |
| 4,897,390 | 1/1990 | Ruhe | 514/177 |
| 4,898,694 | 2/1990 | Schwartz et al. | 260/397.5 |
| 4,902,680 | 2/1990 | Aroonsakul | 514/171 |
| 4,959,358 | 9/1990 | Carey et al. | 514/171 |
| 5,011,678 | 4/1991 | Wang et al. | 424/45 |
| 5,028,631 | 7/1991 | Schwartz et al. | 514/691 |
| 5,030,739 | 7/1991 | Foricher et al. | 552/542 |
| 5,077,284 | 12/1991 | Loria et al. | 514/171 |
| 5,206,008 | 4/1993 | Loria | 424/45 |
| 5,277,907 | 1/1994 | Loria | 424/93 |

FOREIGN PATENT DOCUMENTS

| | | |
|---|---|---|
| 0133995 | 3/1985 | European Pat. Off. . |
| 0210665 | 4/1987 | European Pat. Off. . |
| 0246650 | 11/1987 | European Pat. Off. . |

OTHER PUBLICATIONS

Brochure entitled "Instructions For Weld–Splicing" Eagle Urethane Belting Eagle Belting Company, 1683 Souoth Mt. Prospect Road, Des Plaines, IL 60018 1977.

The Faseb Journal, Abstracts, vol. 2, No. 4, Mar. 15, 1988.

Biochem, IUPAC–IUB Joint Commission on Biochemical Nomenclature (JCBN), 1989, The nomenclature of steriods.

Schauer, Rohrer, Hanson, Lardy & Stratman, "β agonist; in Hormones Thermogenesis and Obesity", 1989, Elsevier, N.Y. pp. 485–501.

Lardy, et al., "Dehydroepiandrosterone Induces Enzymes That Permit Thermogenesis and Decrease Metabolic Efficiency," Hormones, Thermogenesis and Obesity (1989), pp. 415–426.

Partridge & Lardy, 1989, Cell Bio. 107:203A, Carbohydrate Chemistry and Metabolism.

Nestler, Barlascini, Clore & Blackard, 1989, Hormones, Thermogenesis & Obesity, Dehrdroepiandrosterones Effects on Insulin Sensitivity Serum Lipid Levels, and Body Composition in Normal Men, pp. 405–414.

Vec, Lopez, The Lancet, Dec. 2, 1989, pp. 1335–1336, Antiglucocorticoid Actions of Dehydroepiandrosterone and Low Concertrations in Alzeimher's Disease.

Lardy, Stratman, 1989, Hormones, Thermogenesis & Obesity, pp. 427–439, Up–Regulation of the Immune Response and Resistance to Virus Infection Dehydroepiandrosterone (DHEA).

Evans, Articles, May 13, 1988, The Steroid and Thyroid Hormone Receptor Superfamily, pp. 889–895.

Flood & Roberts, 1988, Elsevier Science Publishers, pp. 178–181, Dehydroepiandrosterone Sulfate Improves Memory in aging mice.

Chasalow, Blethen, Tobash Myles & Butler, 1987, American Journal of Medical Genetics, Steroid Metabolic Disturbances in Prader–Willi Syndrome, pp. 857–864.

Bailey, Day, Bray, Lipson & Flatt, Dec. 19, 1984, Georg Thieme Venlag Stuttgart Role of Adrenal Glands in the Development of Abnormal Glueose and Insulin Homeostasis in Genetically Obese (ob/ob) Mice, pp. 357–360.

Chasalow, Blethen & Taysi, Oct. & Nov. 1985, pp. 827–843, Steroids, Possible Abnormalities of Steroid Secretion in Children with Smith–Lemli–Opitz Syndrome and Their Parents.

Coleman, Leiter & Schwizer, Jun. 17, 1982, pp. 830–833, Rapid Publications, Therapeutic Effects of Dehyroepiandrosterone (DHEA).

Schwartz & Tannen, vol. 2, No. 12, 1981, pp. 1335–1337, Carinogenesis Inhibition of 7,12–dimethylbenz[a]anthracene– and urethan–induced lung tumor formation in A/J mice by long–term treatment with dehydroepiandrosterone.

Schwartz, Mar. 1979, Cancer Research, pp. 1129–1131, Inhibition of Spontaneous Breast Cancer Formation in Female C3H (A ry/a) Mice by long Term Treatment with Dehydroepaindrosterone.

Yen, Allan, Pearson, Acton and Greenberg, Lipids, vol. 12, 1977, pp. 409–413, Prevention of obesity in Avy/a Mice By Dehydroepiandrosterone.

(List continued on next page.)

Primary Examiner—Theodore J. Criares
Attorney, Agent, or Firm—Michael S. Sherrill

[57] ABSTRACT

Immune system response may be enhanced by administering a Δ5-Androstene-3β-ol-17-one having a $C_7$ substituent selected from the group consisting of oxo, hydroxy and groups convertible thereto by hydrolysis.

4 Claims, No Drawings

OTHER PUBLICATIONS

Gardner, 1974, Academic Press, Inc., A Sensitive Colorimetric Assay for Mitochondrial α Glycerophosphate Dehydrogenase.

Lee & Lardy, Mar. 1965, vol. 240, No. 3, The Journal of Biological Chemistry, Influence of Thyroid Hormones on L–Alpa–Glycerophosphate Dehydrogenases and Other Dehydrogenases in Various Organs of the Rat.

Dodson, Nicholson & Muir, Dec. 5, 1959, pp. 6295–6299, Oxidation of Dehydroisoandrosterone at C–7.

Lee, Takemori & Lardy, vol. 234, No. 11, Nov. 1959, The Journal of Biological Chemistry, Enhanced Oxidation of α–Glycerophosphate by Mitochondria of Thyroid–fed Rats, pp. 3051–3053.

Gordon, Shantz & Talalay, The Johns Hopkins University School of Medicine Modulation of Growth, Differentiation and Carcinogenesis by Dehydroepiandrosterone, pp. 355–382 (1982).

Effect of Dehydroepiandrosterone Treatment on Liver Metabolism in Rats, Margot P. Cleary, *The International Journal of Biochemistry*, vol. 22, No. 3, pp. 205–120, 1990.

Anti–Obesity Effect of Two Differet Levels of Dehydroepiandrosterone in Lean and Obese Middle–Aged Female Zucker Rats, Margot P. Cleary and Joseph F. Zisk, *International Journal of Obesity* (1986) vol. 10, pp. 193–204.

Effects of Dietary Dehydroepiandrosterone on Body Weight and Food Consumption in Lethal Yellow ($A^y/A^w$) and White–Bellied Agouti ($A^w/A^w$) Mice (Strain 129/Sv), Lisa D. Staber, Nels H. Granholm, Peter J. Wilkin, *Proceedings of the South Dakota Academy of Science*, vol. 62 (1983), pp. 154–162.

Kalimi, Opoku, Lu, Yanal, Khalid, Regelson & Qureshi, Studies on the Biochemical Action and Mechanism of Dehydroepiandrosterone, 1990, Walter de Gruyter & Co.

Yuan Su and Lardy, Dehydroepiandrosterone–responsive Enzyme Induction in Rat Liver, J. Biochemistry 110:207–213 (1991).

TREATMENT OF IMMUNE SYSTEM WITH Δ5-ANDROSTENES

This is a continuation-in-part of U.S. patent application Ser. No. 922,850 filed Jul. 31, 1992 now U.S. Pat. No. 5,292,730, which is a continuation-in-part of U.S. patent application Ser. No. 867,288 filed Apr. 10, 1992 now U.S. Pat. No. 5,296,481, which is a continuation of U.S. patent application Ser. No. 575,156 filed Aug. 29, 1990 abandoned.

FIELD OF THE INVENTION

Broadly, the invention relates to the use of steroids for effecting a desired biological response. Specifically, the invention relates to the use of Δ5-androstenes for improving antibody responsiveness of the immune system.

BACKGROUND

Living animals have an immune system which protects them against the introduction and advancement of pathogenic microorganisms. Upon detection of an antigen, such as a pathogenic microorganism, T cells are activated to produce lymphokines that influence the activities of other host cells while B cells are stimulated to mature and produce immunoglobulins or antibodies that react with the antigen.

The effectiveness of the immune system depends upon several factors including the specific pathogenic microorganism and the vitality of the immune system. Certain pathogenic microorganism are capable of reducing immune system activity while others are capable of overcoming the normal responsiveness of the system.

Immune senescence is a decrease in the antibody responsiveness of the immune system which retards the ability of the system to immunize the body against pathogenic microorganisms. Such a depressed immune system results in an increase in the frequency and severity of pathogenically induced maladies and possibly death.

Immune senescence may result as a natural consequence of aging or as a deleterious effect of pathological microorganism(s). Immune senescence is one of the major health problems of our time with a general consensus and within the medical profession that the problem may soon reach epidemic proportions.

Loria et al. (U.S. Pat. No. 5,077,284) discloses that administration of dehydroepiandrosterone (DHEA) (Δ5-Androstene-3-ol-17-one) can improve a host's response to viral infections. Unfortunately, DHEA also stimulates the production of sex hormones to such an extent that it is generally considered unsuitable for use as a therapeutic agent. The Loria et al. patent itself acknowledges this drawback at column 2, lines 21–27. Loria et al. attempts to dismiss this drawback by suggesting that the side effect may be overcome by monitoring the dose and/or using analogs. Unfortunately, others have been unable to overcome the side effect by the methods suggested by Loria et al. and Loria et al. does not suggest any specific dosage manipulations or analogs which could be used.

It is widely recognized that steroid hormones exhibit "structurally specific" activity such that minor changes in structure, including the addition, deletion and/or substitution of single substituent groups, frequently alters the biological activity of the steroid. See, *Ortho Pharmaceutical Corp. v. Smith*, 959 F.2d 936, 943, 22 U.S.P.Q.2d 1119, 1125 (Fed. Cir. 1992). Adjacent steroid homologs cannot be presumed to possess the same utility due to the greater unpredictability of compounds in that field. *Brenner v. Manson*, 383 U.S. 519, 532, 148 U.S.P.Q. 689, 694 (1966). Essentially identical structures are generally required before one skilled in the art would be inclined to believe that two steroids would possess the same properties or characteristics.

This "structurally specific" activity of steroids has frustrated attempts to locate a derivative of DHEA which exhibits the desired biological response without the undesired side effects.

Accordingly, a substantial need exists for a therapeutic agent effective for enhancing the responsiveness of the immune system against the invasion of pathological microorganisms.

SUMMARY OF THE INVENTION

Immune Response

Responsiveness of the immune system may be enhanced by administering a therapeutic amount of Δ5-Androstene-3β-ol-17-dione having a $C_7$ substituent selected from the group consisting of oxo, hydroxy and groups convertible thereto by hydrolysis.

These steroids are particularly effective for up-regulating the immune system as they, contrary to other Δ5-Androstenes, provide the desired biological response without stimulating the undesired production of additional sex hormones.

DETAILED DESCRIPTION OF THE INVENTION INCLUDING A BEST MODE

Responsiveness of the immune system may be enhanced by administering a Δ5-Androstene-3β-ol-17-one having a $C_7$ substituent selected from the group consisting of oxo, hydroxy and groups convertible thereto by hydrolysis.

These steroids may also be administered as a carbamate, enanthate or other ester derivative as such derivatives are capable of releasing the specified steroid within the intestinal tract, blood and/or body tissues.

Synthesis (1) Δ5-Androstene 3β,7-diol, 17-one (7-hydroxy DHEA)

Δ5-Androstene 3β,7α-diol, 17-one (7-hydroxy DHEA) can be synthesized from commercially available DHEA acetate (10) by sequentially synthesizing:

Δ5-Androstene-3β hydroxy-17-one acetate Δ5-Androstene-3β-hydroxy-7-bromo-17-one acetate Δ5-Androstene-3β,7α-hydroxy-17-one diacetate Δ5-Androstene-3β,7α-hydroxy-17-one Δ5-Androstene 3β-hydroxy-7-bromo-17-one (7-bromo DHEA) can be synthesized from Δ5-Androstene 3β-hydroxy-17-one acetate (DHEA acetate) by reacting the DHEA acetate with a brominating agent such as Dibromantin (1,3 dibromo 5,5 dimethylhydantoin or N-bromo succinimide. The 7-bromo DHEA is unstable and must be used immediately in the next step of the process.

The 7-bromo DHEA containing an isomeric mixture of 7α-bromo DHEA and 7β-bromo DHEA may be equilibrated to 7α-bromo DHEA in accordance with the method described for a cholesterol derivative in Confalone, P. N., Kulesha, I. D., and Uskokovic, M. R. *Jour. Org. Chem.*, vol. 46, pp 1030–1032 (1981). Briefly the racemic mixture of 7-bromo DHEA is contacted with cold anhydrous LiBr and shielded from light until the stereospecific composition is achieved.

Δ5-androstene 3β, 7-hydroxy-17-one diacetate (7-hydroxy DHEA diacetate) may be synthesized from the 7-bromo DHEA by reacting the 7-bromo DHEA with a mixture of glacial acetic acid and powdered silver acetate at room temperature in a suitable solvent such as methylene chloride or acetone.

Δ5-androstene 3β, 7α-hydroxy-17-one (7α-hydroxy DHEA) may be synthesized from the 7-hydroxy DHEA diacetate by reacting the 7α-hydroxy DHEA diacetate dissolved in methanol with an aqueous solution containing a suitable base such as $Na_2CO_3$.

The synthesized 7-hydroxy DHEA may then be purified by (i) evaporating the methanol in vacuo, (ii) extracting the 7-hydroxy DHEA into an appropriate organic solvent such as dichloromethane, (iii) evaporating the organic solvent in vacuo, (iv) azeotropically drying the extracted solids containing the 7-hydroxy DHEA with a suitable organic solvent such as ethanol, (v) dissolving the extracted solids in acetone, and then (vi) adding a suitable precipitating agent, such as hexane, to the acetone solution to produce purified crystals of Δ5-Androstene 3β,7α-diol, 17-one (7-hydroxy DHEA).

A second crop of Δ5-Androstene-3β,7α-diol-17-one (7-hydroxy DHEA) crystals may be obtained by cooling the resultant solution below room temperature.

(2) Δ5-Androstene-3β-ol-7,17-dione (7-keto DHEA)

Δ5-Androstene 3β-ol-7,17-dione can be synthesized from commercially available DHEA acetate by sequentially synthesizing:

3β-acetoxy-Δ5-androstene-17-one   3β-acetoxy-Δ5-androstene-7,17-dione   Δ5-androstene 3β-hydroxy-7,17-dione 3β-acetoxy-Δ5-androstene-7,17-dione (7-oxo DHEA acetate) can be synthesized from 3β-acetoxy-Δ5-androstene-17-one (DHEA acetate) by reacting the DHEA acetate with the oxidizing agent $CrO_3$ in accordance with the procedure outlined in Fieser, L. F., *Jour. Am. Chem. Soc.*, vol. 75, pp 4386–4394 (1953).

Δ5-androstene 3β-hydroxy-7,17-dione (7-one DHEA) can be synthesized from the 7-one DHEA acetate and purified by employing the deesterification and purification steps set forth above with respect to the synthesis and purification of 7-hydroxy DHEA from 7hydroxy DHEA diacetate.

Treatment

A subject may be treated with the steroids specified herein by any of the commonly accepted practices including subcutaneous injection, transdermal injection, intradermal injection, oral or nasal. It is believed that treatment at a dosage rate of about 0.1 to 2 grams of steroid per 100 kilograms of body weight per day, preferably 0.5 to 2 grams of steroid per 100 kilograms of bodyweight per day, is generally effective for triggering the desired biological responses. A dose rate of less than about 0.1 grams per 100 kilograms bodyweight is generally believed to be insufficient to trigger the desired biological response while a dose rate of greater than about 2 grams per 100 kilograms bodyweight is believed to result in an increase in the cost of the treatment without providing a corresponding benefit in performance. The optimum dose rate to be administered to a subject is case specific as the optimum dose rate depends upon several factors including body composition, age, and the like.

Without intending to be limited thereby, we believe that the steroids specified herein enhance performance of the immune system by interfering with the immunosuppressive action of glucocorticoids.

A subject may be treated with one of the steroids specified herein on substantially any desired schedule with the treatment prophylactic (prior to infection) or curative (after infection) in nature. However, it is believed that the steroids themselves are not stored within the body and are substantially removed and/or deactivated within hours after administration. Accordingly, for optimum effectiveness the subject under treatment should be treated at least once a day. For reasons of convenience, the subject under treatment may be treated less frequently, such as every other day or once a week, when less than maximum performance is acceptable.

As is apparent from the factors which affect dosage and dose rate, each particular subject should be carefully and frequently reviewed and the dosage and/or dose rate altered in accordance with the particular situation.

The treatement is effect against a variety of infectious agents including RNA viral, DNA viral, bacterial, fungal, parasitic, and prion.

Experimental

Example I

Synthesis

Δ5-Androstene 3β,7α-diol-17-one (7-hydroxy DHEA)

(Step 1) Into a two liter, triple neck, round bottom flask equipped with a magnetic stirrer and a reflux condenser was placed 1000 ml hexane (b.p 69–71°), 10 grams (0.03 moles) DHEA acetate and 13.6 grams (0.16 moles) $NaHCO_3$ to form a first mixture. The first mixture was placed under a $N_2$ atmosphere and heated under constant agitation to reflux. Into the refluxing first mixture was added 6.11 grams (0.021 moles) Dibromantin (1,3 dibromo 5,5 dimethylhydantion) as a brominating agent to form a second solution. The second solution gradually turned orange after which it rapidly turned a pale white/yellow. The second solution was refluxed for 30 minutes, cooled to room temperature and filtered through a sintered glass funnel. The residue was rinsed with 50 ml dichloromethane and the combined filtrate rotovapped to dryness at a temperature of less than 35° C. The dry filtrate (Δ5-Androstene 3β-ol-7-bromo-17-one) is unstable to storage and was used immediately in step two.

(Step 2) The dry filtrate was resolubilized in 80 ml of dichloromethane in a one liter stoppered flask equipped with a magnetic stirrer and placed in an ice bath. Into the resolubilized filtrate was added 8 grams anhydrous LiBr in 320 ml ice-cold acetone to form a third solution. The third solution was shielded from light and stirred continuously for three hours. The resulting solution containing predominantly Δ5-Androstene 3β-ol-7α-bromo-17-one was allowed to warm briefly and used immediately in step three.

(Step 3) Into a 500 ml flask equipped with a magnetic stirrer was placed 320 ml dichloromethane, 80 ml glacial acetic acid, and 26 grams of silver acetate to form a first suspension. The first suspension was stirred continuously for 20 minutes at room temperature. The stirred first suspension was added under constant agitation into the solution of predominantly Δ5-Androstene 3β-ol-7α-bromo-17-one to form a second suspension. The second suspension was constantly stirred for 30 minutes at room temperature after which the suspension was filtered through a sintered glass funnel to separate a solid fraction. The filtered solid fraction was rinsed with 100 ml dichloromethane. The filtrate was extracted three times with 1000 ml of water, remaining acetic acid was neutralized with 5% NaHCO$_3$ solution, and the dichloromethane solution was extracted twice more with water. The organic solution containing Δ5-Androstene 3β-17α-diol-17-one diacetate was then rotovapped to dryness.

(Step 4) The dried extracted solids were resolubilized in 500 ml methanol in a one liter, triple necked flask equipped with a magnetic stirrer and a reflux condenser to form a fourth solution. The fourth solution was placed under a N$_2$ atmosphere and heated under constant stirring to reflux. Into the fourth solution was added 250 ml of a 5% aqueous solution of Na$_2$CO$_3$ to form a fifth solution. The fifth solution was refluxed under constant agitation for 45 minutes. The methanol was rotovapped off and the aqueous fifth solution carefully brought to a pH of 7 with an appropriate amount of glacial acetic acid. The neutralized fifth solution was extracted twice with 100 ml of dichloromethane. The dichloromethane solution of Δ5-Androstene 3β,7α-diol-17-one was rotovapped to near dryness, azeotropically dried with absolute ethanol, and then azeotropically dried twice with acetone. Warm acetone was added to the dried extracted solids until the solids were completely dissolved to form a sixth solution. Hexane was added to the sixth solution until the solution began to cloud at which time crystals of Δ5-Androstene 3β-7α-diol-17-one began to format room temperature.

A second crop of Δ5-Androstene 3β-7α-diol-17-one crystals was obtained by cooling the remaining sixth solution.

The product melts at about 187°–189° C. and when recrystallized from acetone/hexane melts at about 192°–193° C.

Example II

Synthesis

Δ5-Androstene 3β- 7(αβ)-diol-17-one 7αβ-hydroxy DHEA

Δ5-Androstene 3β-7α-diol-17-one was manufactured in accordance with the procedure set forth in Example I except that Step 2 was omited and the dried filtrate from Step I simply resolubilized in the 80 ml of dichloromethane in preparation for Step 3.

Example III

Synthesis

Δ5-Androstene 3β-ol-7,17-dione 7-keto DHEA (Step 1) Into a 50 ml flask equipped with a magnetic stirrer and a water bath was placed 6.5 ml acetic anhydride, 23 ml acetic acid, 1.7 grams sodium acetate, and 2 grams DHEA acetate to form a first mixture. Into the first mixture was added 2 grams chromium trioxide over a thirty minute period to form a second mixture. The first mixture was maintained at a constant temperature of 56°–58° C. and continuously agitated during addition of the chromium trioxide. The second mixture was maintained at 56°–58° C. and continuously agitated for an additional hour after which the second mixture was cooled and slowly poured under continuous agitation into 600 ml of ice water to form a precipitate. The flocculent precipitate was collected on a sintered glass funnel and washed with water until no longer green. After drying in vacuo over P$_2$O$_5$ the product was dissolved in methanol and recrystallized to yield substantially pure Δ5-Androstene 3β-acetoxy-7,17-dione having a melting point of about 191°–192° C.

(Step 2) The precipitate was resolubilized in 500 ml of methanol in a one liter, triple necked, round bottom flask equipped with a magnetic stirrer and reflux condenser to form a third solution. The third solution was placed under a N$_2$ atmosphere and heated under constant agitation to reflux. Into the third solution was added 250 ml of a 5% solution of Na$_2$CO$_3$ to form a fourth solution. The fourth solution was refluxed under constant agitation for 45 minutes. The methanol was rotovapped off and the aqueous fourth solution carefully brought to a pH of 7 with an appropriate amount of glacial acetic acid. The neutralized fourth solution was extracted with two 100 ml portions of dichloromethane, the two portions combined, and the dichloromethane evaporated in vacuo. The extracted solids were then azeotropically dried first with absolute ethanol and then with two separate portions of acetone. Methanol was added to the dried extracted solids until the solids were completely dissolved to form a fifth solution. Hexane was added to the fifth solution until the solution began to cloud at which time crystals of Δ5-Androstene 3β-ol-7,17-dione began to format room temperature.

A second crop of Δ5-Androstene 3β-ol-7,17-dione crystals was obtained by cooling the remaining sixth solution.

The resultant product had a melting point of about 235°–238° C.

Example IV

Synthesis

Δ5-Androstene 3β-ol-7,17-dione 7-keto DHEA

Into a 250 ml flask equipped with a magnetic stirrer and a water bath was placed 4.1 grams N-hydroxyphthalimide and 50 ml acetone to form a first mixture. Into the refluxing first mixture was sequentially added 8.25 grams DHEA acetate and 0.4 grams dibenzoyl peroxide to form a second mixture. A weak stream of compressed air was introduced into the flask and the second mixture refluxed for nine hours. The components should be neat and pure. The presence of any acidic and/or basic impurities increases reaction time and decreases yield.

The refluxed second mixture was cooled to room temperature, evaporated to dryness on a rotary evaporator, and treated with 50 ml tetrachloromethane at 50° C. for 30 minutes to form a white crystalline precipitate of N-hydroxyphthalimide. The N-hydroxyphthalimide precipitate was filtered off under suction after cooling the tetrachloromethane mixture to room temperature, washed with 10 ml tetrachloromethane, and dried under suction to yield 3.8 grams (92.6) N-hydroxyphthalimide suitable for reuse in the process.

The filtrate was evaporated on a rotary evaporator and the oily residue dissolved in 50 ml of pyridine heated to 50° C. to form a third mixture. The third mixture was cooled to 5°–10° C. and treated with 5 ml of acetic anhydride to form a fourth mixture. The fourth mixture was stirred overnight at room temperature and then concentrated on a rotary evaporator.

The residue was suspended in 30 ml of methanol heated to 50° C. The suspension was then cooled in an ice-bath to form a crystalline precipitate and the precipitate suction filtered. The crystals were washed with methanol and dried under suction to yield 5 grams (58%) Δ5-Androstene 3β-ol-7,17-dione having a slightly yellowish tint.

Warm acetone was added to the dried Δ5-Androstene 3β-ol-7,17-dione extracted solids until the solids were completely dissolved to form a fifth mixture. Hexane was added to the fifth mixture until the mixture began to cloud, at which time crystals began to format room temperature to yield 4.3 grams (50%) of white crystalline Δ5-Androstene 3β-ol-7,17-dione. The resultant Δ5-Androstene 3β-ol-7,17-dione had a melting point of 183°–184° C.

Example V

Immunomodulatory Effect of Δ5-Androstene 3β-ol-7,17-dione (7-Oxo DHEA)

Thirty (30) acclimated and Thoren-unit housed one month old Balb/c mice were separated into six (6) groups of five and bled retro-orbitally under Metofane® anesthesia to obtain the pre-vaccination serum. Treatments and doses for all groups are set forth in Table One below. The DHEA utilized in the trials was obtained from Steraloids, Inc. Wilton, New Hampshire. The 7-Oxo DHEA was synthesized by the procedure of Example III.

TABLE ONE

| Group | Treatment Composition | Steroid Dose/# | Treatment Site |
|---|---|---|---|
| A | 7-Oxo-DHEA | 500 μg/2 | Contralateral |
| B | DHEA | 500 μg/2 | Contralateral |
| C | 7-Oxo-DHEA | 5 μg | Ipsilateral |
| D | Olive Oil | 0 | Ipsilateral |
| E | DHEA | 50 μg | Ipsilateral |
| F | 7-Oxo-DHEA | 50 μg | Ipsilateral |

Mice receiving two treatments (/2) received the first treatment three days before vaccination and the second treatment at the time of vaccination. All other treatments were administered at the time of vaccination. The vaccine consisted of 0.17 ml trivalent influenza vaccine (A/Taiwan/H3N2/868, A/Panama/H1N1/91, B/Beijing). Mice were bled three weeks after vaccination to obtain post-vaccination serum.

Determination of the concentration of influenza antibodies in the pre-vaccination and post-vaccination sera were determined by ELISA at dilutions of 1:1000, 1:4000 and 1:16000 with antibody levels reported in optical density at 405 nm with increased optical density indicating increased antibody concentration.

The post vaccination optical density for each group is depicted by dilution in Tables Two (1:1000), Three (1:4000) and Four (1:16000). The baseline optical densities for pre-vaccination sera ranged from values of 0.00 to 0.25 with an average of 0.08. The background optical density averaged 0.1.

TABLE TWO

Optical Density
Post-Vaccination serum
1:1000 Dilution

| Group | Density (Beijing) | Density (Taiwan) | Density (Panama) |
|---|---|---|---|
| A | 2.26 | 1.64 | 1.85 |
| B | 1.25 | 1.59 | 1.76 |
| C | 1.35 | 1.89 | 1.37 |
| D | 0.87 | 1.18 | 1.01 |
| E | 1.71 | 1.44 | 1.17 |
| F | 2.06 | 1.19 | 0.93 |

TABLE THREE

Optical Density
Post-Vaccination serum
1:4000 Dilution

| Group | Beijung | Taiwan | Panama |
|---|---|---|---|
| A | 1.92 | 0.82 | 1.20 |
| B | 0.93 | 0.90 | 1.16 |
| C | 0.85 | 1.43 | 0.64 |
| D | 0.47 | 0.84 | 0.39 |
| E | 1.73 | 0.71 | 0.63 |
| F | 2.25 | 0.61 | 0.35 |

TABLE FOUR

Optical Density
Post-Vaccination serum
1:16000 Dilution

| Group | Beijing | Taiwan | Panama |
|---|---|---|---|
| A | 0.95 | 0.32 | 0.48 |
| B | 0.52 | 0.41 | 0.38 |
| C | 0.38 | 0.35 | 0.27 |
| D | 0.15 | 0.22 | 0.14 |
| E | 0.71 | 0.28 | 0.24 |
| F | 0.99 | 0.23 | 0.09 |

A Bonferroni/Dunn analysis was conducted upon the test results to compare post vaccination antibody responses to combined antigens. The results of this analysis are set forth in Tables Two BD (1:1000), Three BD (1:4000) and Four BD (1:16000).

TABLE TWO BD

Bonferroni/Dunn Analysis
1:1000 Dilution

| Group | Mean Diff. | Crit. Diff. | P-Value |
|---|---|---|---|
| A B | .483 | .953 | .1262 |
| A C | .267 | .953 | .3946 |
| A D | .707 | 1.004 | .0355 |
| A E | .238 | 1.004 | .4709 |
| A F | .180 | 1.004 | .5857 |
| B C | −.216 | .898 | .4650 |
| B D | .223 | .953 | .4760 |
| B E | −.245 | .953 | .4351 |
| B F | −.303 | .953 | .3344 |
| C D | .439 | .953 | .1635 |
| C E | −.029 | .953 | .9266 |
| C F | −.087 | .953 | .7806 |
| D E | −.468 | 1.004 | .1591 |
| D F | −.527 | 1.004 | .1141 |
| E F | −.058 | 1.004 | .8596 |

TABLE THREE BD

Bonferroni/Dunn Analysis
1:4000 Dilution

| Group | Mean Diff. | Crit. Diff. | P-Value |
| --- | --- | --- | --- |
| A B | .493 | .989 | .1326 |
| A C | .219 | .989 | .5004 |
| A D | .597 | 1.043 | .0853 |
| A E | .092 | 1.043 | .7871 |
| A F | −.077 | 1.043 | .8229 |
| B C | −.274 | .933 | .3726 |
| B D | .103 | .989 | .7505 |
| B E | −.401 | .989 | .2202 |
| B F | −.570 | .989 | .0832 |
| C D | .377 | .989 | .2481 |
| C E | −.127 | .989 | .6964 |
| C F | −.296 | .989 | .3639 |
| D E | −.504 | 1.043 | .1446 |
| D F | −.673 | 1.043 | .0529 |
| E F | −.169 | 1.043 | .6217 |

TABLE FOUR BD

Bonferroni/Dunn Analysis
1:16000 Dilution

| Group | Mean Diff. | Crit. Diff. | P-Value |
| --- | --- | --- | --- |
| A B | .132 | .456 | .3810 |
| A C | .178 | .456 | .2384 |
| A D | .322 | .481 | .0452 |
| A E | .063 | .481 | .6886 |
| A F | −.010 | .481 | .9495 |
| B C | .046 | .430 | .7448 |
| B D | .190 | .456 | .2077 |
| B E | −.068 | .456 | .6486 |
| B F | −.142 | .456 | .3461 |
| C D | .144 | .456 | .3383 |
| C E | .114 | .456 | .4465 |
| C F | .188 | .456 | .2133 |
| D E | .258 | .481 | .1057 |
| D F | .332 | .481 | .0391 |
| E F | .073 | .481 | .6427 |

Conclusions

The DHEA and Δ5-Androstene-3β-ol-7,17-dione (7-Oxo DHEA) did not induce clinically apparent toxicity.

The immune response to Taiwan A/H1N1 varied the least between treatment groups. Healthy mice normally respond well to this virus. Accordingly, it appears that treatment with Δ5-Androstene-3β-ol-7,17-dione does not enhance the immune response when the normal immune response is normally "optimally immunogenic".

Δ5-Androstene-3β-ol-7,17-dione contralateral site injection produced the greatest response to the A/Panama/H1N1/91 and B/Beijing viruses. Healthy mice normally do not respond well immunologically to this virus. Accordingly, it appears that treatment with Δ5-Androstene-3β-ol-7,17-dione does enhance the immune response when the normal immune response is less than optimal.

Example VI

Immune System Response of Δ5-Androstene 3β-ol-7,17-dione (7-Oxo DHEA)

Fourty (40) acclimated and Thoren-unit housed five-six week old female Balb/c mice were separated into a control group of ten (10) mice and two groups of fifteen (15) mice. Treatments and doses for all groups are set forth in Table Five below. The DHEA utilized in the trials was obtained from Steraloids, Inc. Wilton, New Hampshire. The 7-Oxo DHEA was synthesized by the procedure of Example IV. Treatments were administered on days "3, −1, +1 and +3 relative to the date of infection. On day zero the mice were intraperitoneally infected with 1–$10^4$ pfu of a lethal strain of Herpes simplex virus. The drugs were suspended in olive oil and administered subcutaneously. The mice were observed for two weeks and scored for mortality over that period. Mortality results are set forth in Table Five.

TABLE FIVE

| Group/ # of Mice | Treatment Composition | Steroid Dose | % Mortality |
| --- | --- | --- | --- |
| AA/10 | Control | 0.1 ml | 80 |
| BB/15 | DHEA | 0.1 ml | 67 |
| CC/15 | 7-Oxo-DHEA | 0.1 ml | 26 |

Conclusions

Administration of Δ5-Androstene-3β-ol-7,17-dione substantially enhances immune response relative to normal response. Δ5-Androstene-3β-ol-7,17-dione is also substantially superior to DHEA in enhancement of immune system response.

What is claimed is:

1. A method for increasing a mammalian immune system's response to infectious agents and immunogens, comprising the step of:
   (a) administering to a mammal identified as susceptible to suffering from a decreased immune system responsiveness therapeutic amount of a Δ5-androstene-3β-ol-17-one steroid having a $C_7$ substituent selected from the group consisting of oxo, hydroxy and groups convertible thereto by hydrolysis, so as to up-regulate the immune system against infection and immunogen.

2. The method of claim 1 wherein the infectious agents include viral, bacterial, fungal, parasitic, veroid and prion.

3. A method for increasing a mammalian immune system's response to infectious agents and immunogens, comprising the step of:
   (a) administering to a mammal in need of such treatment, a therapeutic amount of a Δ5-Androstene-3β-ol-17-one steroid having a $C_7$ substituent selected from the group consisting of oxo, hydroxy and groups convertible thereto by hydrolysis, so as to up-regulate the immune system against infection and immunogen.

4. The method of claim 1 wherein the infectious agents include viral, bacterial, fungal, parasitic, veroid and prion.

* * * * *

UNITED STATES PATENT AND TRADEMARK OFFICE
CERTIFICATE OF CORRECTION

| | | |
|---|---|---|
| PATENT NO. | : | 5,585,371 |
| DATED | : | December 17, 1996 |
| INVENTOR(S) | : | Henry A. Lardy |

It is certified that error appears in the above-identified patent and that said Letters Patent is hereby corrected as shown below:

Col. 3, Line 43, "7hydroxy" should be -- 7-hydroxy --

Col. 5, Line 41, "3β- 7" should be --3β-7 --

Col. 5, Line 45, "omited" should be -- omitted --

Col. 5, Line 45, "Step I" should be -- Step 1 --

Col. 7, Line 12, "format" should be -- form at --

Col. 10, Line 11 ""3" should be -- -3 --

Col. 10, Line 13, "1-10⁴" should be -- $1 \bullet 10^4$ --

Signed and Sealed this

Twenty-fourth Day of June, 1997

Attest:

BRUCE LEHMAN

Attesting Officer

Commissioner of Patents and Trademarks